(12) United States Patent
Weichert et al.

(10) Patent No.: US 6,593,352 B2
(45) Date of Patent: Jul. 15, 2003

(54) SUBSTITUTED ANTHRANILIC ACIDS, THEIR USE AS A MEDICAMENT OR DIAGNOSTIC, AND MEDICAMENT COMPRISING THEM, AND A PHARMACEUTICAL COMBINATION PREPARATION CONTAINING A SODIUM/HYDROGEN EXCHANGE (NHE) BLOCKER

(75) Inventors: Andreas Weichert, Hamburg (DE); Hans-Willi Jansen, Niedernhausen (DE); Heinz-Werner Kleemann, Bischofsheim (DE); Hans-Jochen Lang, Hofheim (DE); Hartmut Rütten, Idstein (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/003,282

(22) Filed: Dec. 6, 2001

(65) Prior Publication Data

US 2002/0123632 A1 Sep. 5, 2002

(30) Foreign Application Priority Data

Dec. 7, 2000 (DE) .......................................... 100 60 809

(51) Int. Cl.⁷ ..................... C07C 311/39; C07D 213/42; C07D 307/52; C07D 333/20; A61K 31/18
(52) U.S. Cl. .......................... 514/357; 514/438; 514/47; 514/562; 546/334; 549/494; 549/76; 562/430
(58) Field of Search ................................ 514/357, 438, 514/471, 562; 546/334; 549/494, 76; 562/430

(56) References Cited

U.S. PATENT DOCUMENTS 3,565,920 A    2/1971  Werner
3,755,383 A  * 8/1973  Feit et al. ................. 260/397.7
3,875,150 A  * 4/1975  Feit et al. ................. 260/239.6

FOREIGN PATENT DOCUMENTS

DE    1 802 208       5/1970
EP    0 604 852 A1    7/1994
EP    0 726 250 A1    8/1996

OTHER PUBLICATIONS

P. Wangemann et al., "Cl⁻–Channel Blockers in The Thick Ascending Limb of The Loop of Henle. Structure Activity Relationship", Pflugers Arch, vol. 407, Suppl. 2, pp. 128–141, (1986).

Derwent Abstract of DE 1 802 208 (1970).

* cited by examiner

*Primary Examiner*—Brian Davis
(74) *Attorney, Agent, or Firm*—Finnegan, Henderson, Farabow, Garrett & Dunner, LLP

(57) ABSTRACT

Substituted anthranilic acids of the formula I

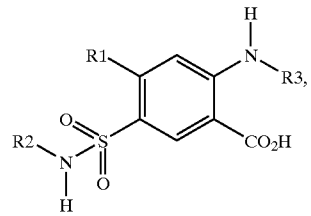

their use as a medicament or diagnostic, and medicament comprising them, and a pharmaceutical combination preparation containing a sodium/hydrogen exchange (NHE) blocker.

16 Claims, No Drawings

SUBSTITUTED ANTHRANILIC ACIDS, THEIR USE AS A MEDICAMENT OR DIAGNOSTIC, AND MEDICAMENT COMPRISING THEM, AND A PHARMACEUTICAL COMBINATION PREPARATION CONTAINING A SODIUM/HYDROGEN EXCHANGE (NHE) BLOCKER

This application claims the benefit of foreign priority under 35 U.S.C. §119 of German patent application no. 10060809.4-43, filed on Dec. 7, 2000 the contents of which are incorporated by reference herein.

The present invention relates to substituted anthranilic acids. In one embodiment, the invention relates to the use of substituted anthranilic acids as a medicament or diagnostic, including a medicament comprising at least one substituted anthranilic acid, and a pharmaceutical combination preparation containing at least one sodium/hydrogen exchange (NHE) blocker and at least one substituted anthranilic acid.

The invention relates to anthranilic acids of the formula I

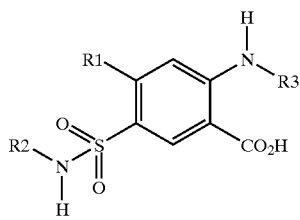

in which:
R(1) is H, Cl, Br, I, CN, $(C_1-C_8)$-alkyl, $(C_3-C_6)$-cycloalkyl, unsubstituted phenyl, or substituted phenyl
  where the substituted phenyl is substituted by 1–3 substituents chosen from F, Cl, $(C_1-C_3)$-alkyl, methoxy and $-(CF_2)_a-CF_3$; and
  where a is zero, 1, 2 or 3;
R(2) is $(C_1-C_8)$-alkyl, $-C_bH_{2b}-(C_3-C_6)$-cycloalkyl, unsubstituted $-C_bH_{2b}$-phenyl, substituted $-C_bH_{2b}$-phenyl, unsubstituted $-C_bH_{2b}$-pyridinyl, substituted $-C_bH_{2b}$-pyridinyl, unsubstituted $-C_bH_{2b}$-thiophenyl, substituted $-C_bH_{2b}$-thiophenyl, unsubstituted $-C_bH_{2b}$-furanyl, or substituted $-C_bH_{2b}$-furanyl
  where the substituted $-C_bH_{2b}$-phenyl, the substituted $-C_bH_{2b}$-pyridinyl, the substituted $-C_bH_{2b}$-thiophenyl, and the substituted $-C_bH_{2b}$-furanyl are each independently substituted by 1–3 substituents chosen from F, Cl, $CF_3$, $(C_1-C_3)$-alkyl, methoxy and $-SO_2NR(4)R(5)$;
  where R(4) and R(5) independently of one another are H or $(C_1-C_4)$-alkyl, and
  where b is zero, 1, 2, 3 or 4;
R(3) is unsubstituted $-C_dH_{2d}$-phenyl or substituted $-C_dH_{2d}$-phenyl,
  where the substituted $-C_dH_{2d}$-phenyl is substituted by 1–3 substituents chosen from F, Cl, $CF_3$, $(C_1-C_3)$-alkyl and methoxy; and
  where d is 3 or 4;
and their pharmaceutically tolerable salts.

In one embodiment, the compounds of formula 1 are those in which:
R(1) is Cl, $(C_1-C_4)$-alkyl, unsubstituted phenyl, or substituted phenyl
  where the substituted phenyl is substituted by 1–3 substituents chosen from F, Cl, $CF_3$, $(C_1-C_3)$-alkyl and methoxy;
R(2) is $(C_1-C_4)$-alkyl, $-C_bH_{2b}$-cyclohexyl, unsubstituted $-C_bH_{2b}$-phenyl, substituted $-C_bH_{2b}$-phenyl, unsubstituted $-C_bH_{2b}$-pyridinyl, substituted $-C_bH_{2b}$-pyridinyl, unsubstituted $-C_bH_{2b}$-thiophenyl, substituted $-C_bH_{2b}$-thiophenyl, unsubstituted $-C_bH_{2b}$-furanyl, or substituted $-C_bH_{2b}$-furanyl
  where the substituted $-C_bH_{2b}$-phenyl, the substituted $-C_bH_{2b}$-pyridinyl, the substituted $-C_bH_{2b}$-thiophenyl, and the substituted $-C_bH_{2b}$-furanyl are each independently substituted by 1–3 substituents chosen from F, Cl, $CF_3$, $(C_1-C_3)$-alkyl, methoxy and $-SO_2NH_2$; and
  where b is zero, 1 or 2;
R(3) is unsubstituted $-n-C_4H_8$-phenyl or substituted $-n-C_4H_8$-phenyl,
  where the substituted $-n-C_4H_8$-phenyl is substituted by 1–3 substituents chosen from F, Cl, $CF_3$, $(C_1-C_3)$-alkyl and methoxy;
and their pharmaceutically tolerable salts.

In another embodiment, the compounds of formula 1 are those in which:
R(1) is Cl, $(C_1-C_4)$-alkyl, unsubstituted phenyl or substituted phenyl,
  where the substituted phenyl is substituted by 1–3 substituents chosen from F, Cl, $CF_3$, $(C_1-C_3)$-alkyl and methoxy;
R(2) is $(C_1-C_4)$-alkyl, $-C_bH_{2b}$-cyclohexyl, unsubstituted $-C_bH_{2b}$-phenyl, substituted $-C_bH_{2b}$-phenyl, unsubstituted $-C_bH_{2b}$-pyridinyl, substituted $-C_bH_{2b}$-pyridinyl, unsubstituted $-C_bH_{2b}$-thiophenyl, substituted $-C_bH_{2b}$-thiophenyl, unsubstituted $-C_bH_{2b}$-furanyl, or substituted $-C_bH_{2b}$-furanyl
  where the substituted $-C_bH_{2b}$-phenyl, the substituted $-C_bH_{2b}$-pyridinyl, the substituted $-C_bH_{2b}$-thiophenyl, and the substituted $-C_bH_{2b}$-furanyl are each independently substituted by 1–3 substituents selected from the group consisting of F, Cl, $CF_3$, $(C_1-C_3)$-alkyl, methoxy or $-SO_2NH_2$; and
  where b is 1;
R(3) is unsubstituted $-n-C_4H_8$-phenyl or substituted $-n-C_4H_8$-phenyl,
  where the substituted $-n-C_4H_8$-phenyl is substituted by 1–3 substituents chosen from F, Cl, $CF_3$, $(C_1-C_3)$-alkyl and methoxy;
and their pharmaceutically tolerable salts.

In one embodiment, the compound of formula 1 may be chosen from 4-chloro-5-(3-chloro-4-fluorobenzylsulfamoyl)-2-phenylbutylaminobenzoic acid, and its pharmaceutically tolerable salts.

In another embodiment, if one of the substituents R(1) to R(5) comprises one or more asymmetric centers, each asymmetric center may independently have either the S or R configuration. Thus, for example, compounds of the invention may be present as optical isomers, as diastereomers, as racemates and as mixtures thereof. Alkyl, as used herein, may be either a straight-chain alkyl group or branched alkyl group.

In one embodiment, compounds of the formula I may be synthesized by the person skilled in the art according to processes known from the literature, including but not limited to:

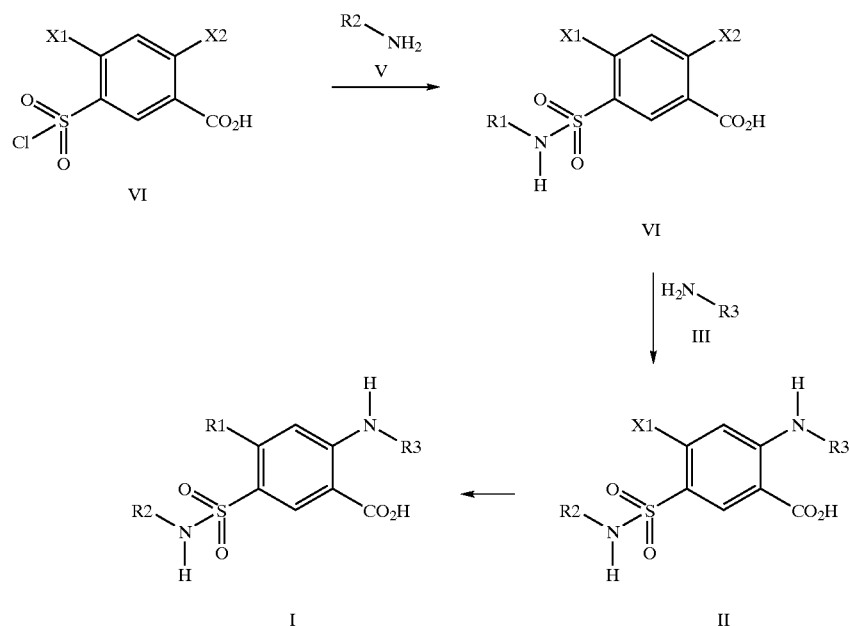

Possible leaving groups, X2 (formula VI), which can be taken into consideration in the nucleophilic aromatic substitution reaction with amines III include, but are not limited to, fluorine and chlorine.

The introduction of some substituents in the 4 position of intermediate II (X1, for example, may be bromine, iodine or —O—SO$_2$CF$_3$) may, in one embodiment, be carried out by methods of palladium-mediated cross-coupling, which are likewise known from the literature, of aryl halides or aryl triflates with, for example, organostannanes, organoboronic acids or organoboranes or organocopper or zinc compounds.

In general, anthranilic acids are weak acids which bind bases with formation of salts. Possible base addition products are all pharmacologically tolerable salts, for example, alkali metal salts, lysinates and tris(hydroxymethyl) methylamine salts.

In one embodiment, the compounds of formula I are substituted anthranilic acids.

A prominent representative of the anthranilic acid class is the furfuryl derivative furosemide, which is used as a diuretic in therapy. Furosemide inhibits the sodium/potassium/2chlorine cotransporter in the ascending branch of Henle's loop in the kidney.

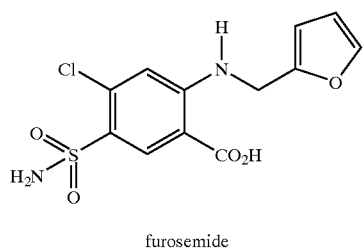

furosemide

DE 18 02 208 describes anthranilic acids which differ from the compounds of the present invention in that they carry an exclusively benzyl, furfuryl or thienyl substituents on R3 and have diuretic action. U.S. Pat. No. 3,565,920 also discloses anthranilic acids that differ from the compounds of the formula I in that they demonstrate a strong salidiuretic activity.

It was therefore surprising that the compounds according to the invention have no undesired and disadvantageous salidiuretic properties, but very good cardioprotective properties, for example in the case of oxygen deficiency symptoms. As a result of their pharmacological properties, the compounds, in one embodiment, are outstandingly suitable as cardioprotective pharmaceuticals for infarct prophylaxis and infarct treatment, and for the treatment of angina pectoris, where they also preventively inhibit or greatly decrease the pathophysiological processes in the formation of ischemically induced damage. Because of their protective actions against pathological hypoxic and ischemic situations, the compounds of the formula I according to the invention may, for example, be used, as a result of inhibition of the cellular Na$^+$/HCO$_3^-$ cotransporter (NBC), as pharmaceuticals for the treatment of all acute or chronic damage caused by ischemia or illnesses induced primarily or secondarily thereby. In one embodiment, this relates to their use as pharmaceuticals for surgical interventions, e.g. in organ transplantation, where the compounds can be used both for the protection of the organs in the donor before and during removal, for the protection of removed organs, for example during treatment with or storage thereof in physiological bath fluids, and during the transfer to the recipient's body.

The compounds may also be useful pharmaceuticals having a protective action when carrying out angioplastic surgical interventions, for example on the heart, and also on peripheral vessels. Moreover, the inventive compounds may reduce the formation or the extent of cardiac insufficiency after various insults.

In another embodiment, corresponding to their protective action against ischemically induced damage, the compounds may be suitable as pharmaceuticals for the treatment of ischemias of the nervous system, in particular of the CNS, where they are suitable, for example, for the treatment of stroke or of cerebral edema. Moreover, the compounds of the formula I according to the invention may likewise be suitable for the treatment of forms of shock, such as of allergic, cardiogenic, hypovolemic and bacterial shock.

In a further embodiment, the compounds of the formula I according to the invention may be distinguished by strong inhibitory action on the proliferation of cells, for example, fibroblast cell proliferation and proliferation of the vascular smooth muscle cells. The compounds of the formula I may therefore be suitable as therapeutics for illnesses in which cell proliferation represents a primary or secondary cause, and may therefore be used as antiatherosclerotics, agents against diabetic late complications, carcinomatous conditions, fibrotic conditions such as pulmonary fibrosis, fibrosis of the liver or fibrosis of the kidneys, organ hypertrophies and hyperplasias, in particular in prostate hyperplasia or prostate hypertropy.

The invention, in one embodiment, relates to a combination of an NBC blocker of formula I with sodium/hydrogen exchange (NHE) inhibitors. In combined therapeutic administration, both classes of active compound surprisingly exhibit synergistic effects in the treatment of syndromes which are to be attributed to ischemic conditions and reperfusion effects. The combinations of an NBC inhibitor with an NHE blocker may thus be suitable for infarct and reinfarct prophylaxis and infarct treatment, and for the treatment of angina pectoris and the inhibition of ischemically induced cardiac arrhythmias, tachycardia and the formation and maintenance of ventricular fibrillation. The combination may also preventively inhibit or greatly decrease the pathophysiological processes in the formation of ischemically induced damage.

Because of their increased protective actions against pathological hypoxic and ischemic situations, the combinations according to the invention may be used, for example, as a result of increased inhibition of the Na$^+$ influx into the cell, as pharmaceuticals for the treatment of acute or chronic damage caused by ischemia or illnesses induced primarily or secondarily thereby. This may relate to their use as pharmaceuticals for surgical interventions, e.g. in organ transplantation, where the combinations of an NHE inhibitor with a blocker of the noninactivating sodium channel may be used both for the protection of the organs in the donor before and during removal, for the protection of removed organs, for example even during their storage in physiological bath fluids, and during transfer to the recipient's body.

The combinations of an NBC blocker of the formula I with NHE inhibitors may be useful pharmaceuticals having a protective action when carrying out angioplastic surgical interventions, for example on the heart, and on peripheral vessels. Corresponding to their protective action against ischemically induced damage, these combinations may also be suitable as pharmaceuticals for the treatment of ischemias of the nervous system, in particular of the central nervous system, where they are suitable for the treatment of stroke or of cerebral edema. Moreover, the combinations according to the invention may likewise be suitable for the treatment of forms of shock, for example of allergic, cardiogenic, hypovolemic and bacterial shock.

It was thus, for example, surprisingly found that the combination of the NBC blocker 4-chloro-5-(3-chloro-4-fluorobenzylsulfamoyl)-2-phenylbutylaminobenzoic acid with the NHE inhibitor cariporide mesilate,

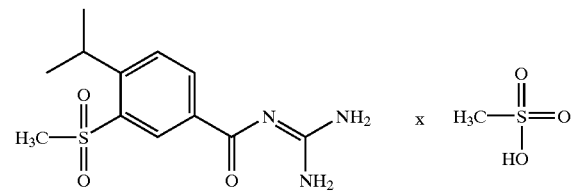

which is described, for example, in U.S. Pat. No. 5,591,754, exhibited a greater than additive cardioprotective action in an ischemia/reperfusion model (isolated beating rat heart).

Pharmaceuticals which contain a compound of formula I may, for example, be administered orally, parenterally, intravenously, rectally or by inhalation, the preferred administration, in one embodiment, may depend on the respective clinical picture of the condition. The compounds of formula I may also be used here on their own or together with pharmaceutical excipients, mainly both in veterinary and human medicine.

The person skilled in the art is familiar on the basis of his/her expert knowledge with excipients which are suitable for the desired pharmaceutical formulation. In addition to solvents, gel formers, suppository bases, tablet excipients, and other excipients, it is possible to use, for example, antioxidants, dispersants, emulsifiers, antifoams, flavor corrigents, preservatives, solubilizers or colorants.

For a form for oral administration, for example, the active compounds may be mixed with the additives suitable therefor, such as vehicles, stabilizers or inert diluents, and brought by means of the customary methods into the suitable administration forms, such as tablets, coated tablets, hard gelatin capsules, aqueous, alcoholic or oily solutions. Inert carriers which can be used are, for example, gum arabic, magnesia, magnesium carbonate, potassium phosphate, lactose, glucose or starch, in particular cornstarch. In this case, preparation may, for example, take place both as dry and as moist granules. Suitable oily vehicles or solvents are, for example, vegetable or animal oils, such as sunflower oil or cod liver oil.

For subcutaneous or intravenous administration, for example, the active compounds may be brought into solution, suspension or emulsion, if desired, using the substances customary therefor such as solubilizers, emulsifiers or further excipients. Possible solvents are, for example: water, physiological saline solution or alcohols, e.g. ethanol, propanol, glycerol, in addition also sugar solutions such as glucose or mannitol solutions, or alternatively a mixture of the various solvents mentioned.

Suitable pharmaceutical formulations for administration in the form of aerosols or sprays are, for example, solutions, suspensions or emulsions of the active compound of the formula I in a pharmaceutically acceptable solvent, such as, in particular, ethanol or water, or a mixture of such solvents.

If required, the formulation may also contain still other pharmaceutical excipients, such as surfactants, emulsifiers and stabilizers, and a propellant. In one embodiment, such a preparation may contain the active compound in a concentration of about 0.1 to about 10, in particular of approximately 0.3 to 3.0% by weight.

The dose of the active compound of formula I to be administered and the frequency of administration depend on the potency and duration of action of the compounds used; moreover also on the nature and severity of the illness to be treated and on the sex, age and weight and individual responsiveness of the mammal to be treated.

On average, the daily dose of a compound of the formula I, in one embodiment, in the case of a patient weighing approximately 75 kg is at least 0.001 mg active to kg of body weight (mg/kg), such as 0.01 mg/kg to 10 mg/kg, such as, for example, 1 mg/kg. In another embodiment, in the case of acute episodes of the illness, for example immediately after suffering a cardiac infarct, even higher and especially more frequent doses may also be necessary, e.g. up to 4 individual doses per day. In particular in the case of i.v. administration, for example in the case of an infarct patient in the intensive care unit, up to 200 mg per day may be necessary.

Experimental Section

List of Abbreviations

| ACN | Acetonitrile |
|---|---|
| HPLC | High pressure liquid chromatography |
| solv. | Solvent |
| RT | Room temperature |
| EA | Ethyl acetate (EtOAc) |
| M.p. | Melting point |
| eq. | Equivalent |
| TFA | Trifluoroacetic acid |
| Rt | Retention time |
| MS | Mass spectrometer |
| dppf | 1,1'-Bis(diphenylphosphino)ferrocene |

Analytical System

HPLC 1 Agilent 1100

Method gradient: 10% ACN (0.1% TFA)/90% water (0.1% TFA) to

90% ACN (0.1% TFA)/10% water (0.1% TFA) in 7 min, 2.5 ml/min

Column: Altech RP18, 3 µm, 7×35 mm

MS: Waters Mass Lynx—ESI-TOF, [M–H$^+$]$^-$, 100% peak, if not stated otherwise

HPLC 2 Agilent 1100 LC/MSD

Method gradient: 5% ACN (0.05% TFA)/95% water (0.05% TFA) to

95% ACN (0.05% TFA)/5% water (0.05% TFA) in 4 min, flow 0.5 ml/min

Column: ESI, [M+H$^+$]$^+$, Merck Purospher RP18, 5 µm, 2×55 mm

Example of a General Procedure for the Preparation of Anthranilic Acids (I/II)

Stage 1: 1.0 eq. of the 2,4-bis-halo-5-chlorosulfonylbenzoic acid of the formula VI is dissolved or suspended in ethyl acetate (5 ml/mmol) and then treated with 5 eq. of amine of the formula V. After stirring for 17 hours at RT, the reaction mixture is acidified to pH 1 to 2 using 2N hydrochloric acid and extracted with EA. After drying over MgSO$_4$, the solv. is evaporated and the crude product is employed in the next stage without further purification.

Stage 2: 1.0 eq. of the 2,4-bis-halo-5-sulfamoylbenzoic acid derivative of the formula IV is treated with 5 eq. of amine of the formula III and heated at 100° C. for 24 hours. After cooling the reaction mixture, it is treated with 5N citric acid solution and extracted with EA. The organic phase is concentrated and the crude product obtained is purified by means of preparative HPLC (RP gel, eluent acetonitrile/water gradient).

EXAMPLE 1

4-Chloro-5-(3-chloro-4-fluorobenzylsulfamoyl)-2-phenylbutylaminobenzoic acid,

Lysine salt, HPLC2: Rt=5.252 MS: 525.20

Synthesis Route a) 4-Chloro-5-(3-chloro-4-fluorobenzylsulfamoyl)-2-chlorobenzoic acid from reaction of 4-chloro-5-(chlorosulfonyl)-2-chlorobenzoic acid and 4-fluoro-3-chlorobenzylamine according to general procedure, stage 1.

b) 4-Chloro-5-(3-chloro-4-fluorobenzylsulfamoyl)-2-phenylbutylaminobenzoic acid a) by reaction with phenylbutylamine according to general procedure, stage 2, colorless crystals.

c) Salt formation with 1 eq. of 1 b), dissolved in acetonitrile, with addition of an aqueous solution of 1 eq. of D, Lysine. After freeze-drying a colorless solid remains.

EXAMPLE 2

4-Bromo-5-(3-chloro-4-fluorobenzylsulfamoyl)-2-phenylbutylaminobenzoic acid,

HPLC2: Rt=5.270 MS: 569.00

Synthesis Route a) 4-Bromo-5-(chlorosulfonyl)-2-chlorobenzoic acid from 4-bromo-2-chlorobenzoic acid by reaction in pure chlorosulfonic acid (10 eq.) at 95° C. in the course of 6 h. After cooling, the mixture is poured onto ice and the precipitate is filtered off, colorless solid.

b) 4-Bromo-5-(3-chloro-4-fluorobenzylsulfamoyl)-2-chlorobenzoic acid from 2a) according to general procedure, stage 1.

c) 4-Bromo-5-(3-chloro-4-fluorobenzylsulfamoyl)-2-phenylbutylaminobenzoic acid from b) by reaction with phenylbutylamine according to general procedure, stage 2, colorless solid.

EXAMPLE 3

5-(3-Chloro-4-fluorobenzylsulfamoyl)-2-phenylbutylaminobenzoic acid,

HPLC2: Rt=5.227 MS: 491.40

Synthesis Route a) 5-(3-Chloro-4-fluorobenzylsulfamoyl)-2-phenylbutylaminobenzoic acid from 2c) by hydrogenolysis by means of 10%-Pd/C catalyst in ethanol at RT for 2 days. The catalyst is filtered off and the solv. is stripped off. Purification is carried out by preparative RPHPLC (water/acetonitrile gradient), colorless solid after freeze-drying.

EXAMPLE 4

4-Methyl-5-(3-chloro-4-fluorobenzylsulfamoyl)-2-phenylbutylaminobenzoic acid,

HPLC2: Rt=5.199 MS: 505.05

Synthesis Route a) Methyl 4-bromo-2-fluorobenzoate from 4-bromo-2-fluorobenzoate by esterification with an excess of acetyl chloride in methanol at RT in the course of 7 h. Aqueous work-up and subsequent freeze-drying yields a colorless solid.

b) Ethyl 4-methyl-2-fluorobenzoate from 1 eq. of 4 a) by reaction with 2 eq. of methylzinc chloride, prepared from the corresponding Grignard reagent in THF and zinc chloride-THF complex, in the presence of 5 mol % of Pd(dppf)Cl$_2$ and 6 mol % of CuI in THF at RT in the course of 18 h. After NH$_4$Cl work-up, the mixture is extracted with EA, the solv. is evaporated, the crude product is purified by means of prep. HPLC and lyophilized, colorless solid.

c) 4-Methyl-2-fluorobenzoic acid from 4 b) by hydrolysis with 2N sodium hydroxide solution in methanol at 50° C. in the course of one hour. Subsequent acidification with 2N hydrochloric acid, extraction with EA and drying over MgSO$_4$ affords a crude product which is employed in the next stage.

d) 4-Methyl-5-(chlorosulfonyl)-2-fluorobenzoic acid from 4 c) by reaction in pure chlorosulfonic acid (10 eq.) at 95° C. in the course of 6 h. After cooling, the mixture is poured onto ice, extracted with EA and dried over MgSO$_4$. Evaporation affords a yellowish oil, which is reacted further in this purity.

e) 4-Methyl-5-(3-chloro-4-fluorobenzylsulfamoyl)-2-fluorobenzoic acid from 4 d) and 4-fluoro-3-chlorobenzylamine analogously to 1 a), colorless solid.

f) 4-Methyl-5-(3-chloro-4-fluorobenzylsulfamoyl)-2-phenylbutylaminobenzoic acid from 4 e) by reaction with phenylbutylamine according to general procedure, stage 2, colorless solid.

EXAMPLE 5

4-isopropyl-5-(3-chloro-4-fluorobenzylsulfamoyl)-2-phenylbutylaminobenzoic acid.

HPLC2: Rt=5.399 MS: 533.10
Synthesis Route
a) Methyl 4-isopropyl-2-fluorobenzoic acid from 1 eq. of 4 a) by reaction with 2 eq. of isopropylzinc chloride, analogously to the preparation of 4 a), colorless solid.
b) 4-Isopropyl-2-fluorobenzoic acid from 5 a) by hydrolysis with 2N sodium hydroxide solution, analogously to 4 c).
c) 4-Isopropyl-5-(chlorosulfonyl)-2-fluorobenzoic acid from 5 b) by reaction in pure chlorosulfonic acid analogously to 4 d).
d) 4-Isopropyl-5-(3-chloro-4-fluorobenzylsulfamoyl)-2-fluorobenzoic acid from 5 c) and 4-fluoro-3-chlorobenzylamine analogously to 1 a), colorless solid.
e) 4-Isopropyl-5-(3-chloro-4-fluorobenzylsulfamoyl)-2-phenylbutylaminobenzoic acid from 5 d) by reaction with phenylbutylamine according to general procedure, stage 2, colorless solid.

EXAMPLE 6

4-n-Propyl-5-(3-chloro-4-fluorobenzylsulfamoyl)-2-phenylbutylaminobenzoic acid,

HPLC2: Rt=5.437 MS: 533.10
Synthesis Route
a) Methyl 4-n-propyl-2-fluorobenzoate from 1 eq. of 4 a) by reaction with 2 eq. of n-propylzinc chloride, analogously to the preparation of 4a), colorless solid.
b) 4-n-Propyl-2-fluorobenzoic acid from 6 a) by hydrolysis with 2N sodium hydroxide solution, analogously to 4 c).
c) 4-n-Propyl-5-(chlorosulfonyl)-2-fluorobenzoic acid from 6 b) by reaction in pure chlorosulfonic acid analogously to 4 d).
d) 4-n-Propyl-5-(3-chloro-4-fluorobenzylsulfamoyl)-2-fluorobenzoic acid from 6 c) and 4-fluoro-3-chlorobenzylamine analogously to 1 a), colorless solid.
e) 4-n-Propyl-5-(3-chloro-4-fluorobenzylsulfamoyl)-2-phenylbutylaminobenzoic acid from 6 d) by reaction with phenylbutylamine according to general procedure, stage 2, colorless solid.

EXAMPLE 7

4-(4-Methylphenyl)-5-(3-chloro-4-fluorobenzylsulfamoyl)-2-phenylbutylaminobenzoic acid HPLC2: Rt=5.762 MS: 581.60
from reaction of 1 eq. 4-bromo-5-(3-chloro-4-fluorobenzylsulfamoyl)-2-phenylbutylaminobenzoic acid and 1.2 eq. of 4-tolylboronic acid in a solv. mixture of toluene/MeOH 2:1 in the presence of 10 mol % of Pd(OAc)$_2$, 20 mol % of triphenylphosphine and 3 eq. of sodium carbonate under reflux for 3 hours. Aqueous work-up, subsequent preparative HPLC and freeze-drying yields a colorless solid.

EXAMPLE 8

4-Chloro-2-phenylbutylamino-5-[(pyridin-4-ylmethyl)sulfamoyl]benzoic acid,

HPLC1: Rt=4.417 MS: 474.1 [M+H+]+
Synthesis Route
a) 2,4-Dichloro-5-[(pyridin-4-ylmethyl)sulfamoyl]benzoic acid from reaction of 2,4-dichloro-5-(chlorosulfonyl)benzoic acid and pyridin-4-ylmethylamine according to general procedure, stage 1.
b) 4-Chloro-2-phenylbutylamino-5-[(pyridin-4-ylmethyl)sulfamoyl]benzoic acid from a) by reaction with phenylbutylamine according to general procedure, stage 2, colorless solid.

EXAMPLE 9

4-Chloro-2-phenylbutylamino-5-[(pyridin-2-ylmethyl)sulfamoyl]benzoic acid

HPLC1: Rt=4.441 MS: 474.1 [M+H+]+
Synthesis Route
a) 2,4-Dichloro-5-[(pyridin-2-ylmethyl)sulfamoyl]benzoic acid from reaction of 2,4-dichloro-5-(chlorosulfonyl)benzoic acid and pyridin-2-ylmethylamine according to general procedure, stage 1.
b) 4-Chloro-2-phenylbutylamino-5-[(pyridin-2-ylmethyl)sulfamoyl]benzoic acid from a) by reaction with phenylbutylamine according to general procedure, stage 2, colorless solid.

EXAMPLE 10

4-Chloro-2-phenylbutylamino-5-(3-chlorobenzylsulfamoyl)benzoic Acid

HPLC1: Rt=5.267 MS: 505.08
Synthesis Route
a) 2,4-Dichloro-5-(3-chloro-4-fluorobenzylsulfamoyl)benzoic acid from reaction of 2,4-dichloro-5-(chlorosulfonyl)benzoic acid and 3-chlorobenzylamine according to general procedure, stage 1.
b) 4-Chloro-2-phenylbutylamino-5-(3-chlorobenzylsulfamoyl)benzoic acid from a) by reaction with phenylbutylamine according to general procedure, stage 2, colorless solid.

EXAMPLE 11

4-Chloro-2-phenylbutylamino-5-(4-sulfamoylbenzylsulfamoyl)benzoic acid

HPLC1: MS: 550.13

Synthesis Route a) 4-Chloro-5-(4-sulfamoylbenzylsulfamoyl)benzoic acid from reaction of 2,4-dichloro-5-(chlorosulfonyl)benzoic acid and 4-sulfamoylbenzylamine according to general procedure, stage 1.
b) 4-Chloro-2-phenylbutylamino-5-(4-sulfamoylbenzylsulfamoyl)benzoic acid from a) by reaction with phenylbutylamine according to general procedure, stage 2, colorless solid.

EXAMPLE 12

4-Chloro-2-phenylbutylamino-5-(2,3-dichlorobenzylsulfamoyl)benzoic acid

HPLC1: Rt=5.368 MS: 539.06

Synthesis Route a) 4-Chloro-5-(2,3-dichlorobenzylsulfamoyl)benzoic acid from reaction of 2,4-dichloro-5-(chlorosulfonyl)benzoic acid and 2,3-dichlorobenzylamine according to general procedure, stage 1.
b) 4-Chloro-2-phenylbutylamino-5-(2,3-dichlorobenzylsulfamoyl)benzoic acid from a) by reaction with phenylbutylamine according to general procedure, stage 2, colorless solid.

EXAMPLE 13

4-Chloro-2-phenylbutylamino-5-(2,4-dichlorobenzylsulfamoyl)benzoic acid

HPLC1: Rt=5.433 MS: 539.06

Synthesis Route a) 4-Chloro-5-(2,4-dichlorobenzylsulfamoyl)benzoic acid from reaction of 2,4-dichloro-5-(chlorosulfonyl)benzoic acid and 2,4-dichlorobenzylamine according to general procedure, stage 1.
b) 4-Chloro-2-phenylbutylamino-5-(2,4-dichlorobenzylsulfamoyl)benzoic acid from a) by reaction with phenylbutylamine according to general procedure, stage 2, colorless solid.

EXAMPLE 14

4-Chloro-2-phenylbutylamino-5-(2-chloro-6-fluorobenzylsulfamoyl)benzoic acid

HPLC1: Rt=5.230 MS: 523.11

Synthesis Route a) 4-Chloro-5-(2-chloro-6-fluorobenzylsulfamoyl)benzoic acid from reaction of 2,4-dichloro-5-(chlorosulfonyl)benzoic acid and 2-chloro-6-fluorobenzylamine according to general procedure, stage 1.
b) 4-Chloro-2-phenylbutylamino-5-(2-chloro-6-fluorobenzylsulfamoyl)benzoic acid from a) by reaction with phenylbutylamine according to general procedure, stage 2, colorless solid.

EXAMPLE 15

4-Chloro-5-[(5-methylfuran-2-ylmethyl)sulfamoyl]-2-phenylbutylaminobenzoic acid

HPLC1: Rt=5.036 MS: 513.19

Synthesis Route a) 2,4-Dichloro-5-[(5-methylfuran-2-ylmethyl)sulfamoyl]benzoic acid from reaction of 2,4-dichloro-5-(chlorosulfonyl)benzoic acid and 5-methylfuran-2-ylmethylamine according to general procedure, stage 1.
b) 4-Chloro-5-[(5-methylfuran-2-ylmethyl)sulfamoyl]-2-phenylbutylaminobenzoic acid from a) by reaction with phenylbutylamine according to general procedure, stage 2, colorless solid.

EXAMPLE 16

4-Chloro-5-[2-(4-chlorophenyl)ethylsulfamoyl]-2-phenylbutylaminobenzoic acid

HPLC1: Rt=5.453 MS: 519.14

Synthesis Route a) 2,4-Dichloro-5-[2-(4-chlorophenyl)ethylsulfamoyl]benzoic acid from reaction of 2,4-dichloro-5-(chlorosulfonyl)benzoic acid and 2-(4-chlorophenyl)ethylamine according to general procedure, stage 1.
b) 4-Chloro-5-[2-(4-chlorophenyl)ethylsulfamoyl]-2-phenylbutylaminobenzoic acid from a) by reaction with phenylbutylamine according to general procedure, stage 2, colorless solid.

EXAMPLE 17

4-Chloro-2-phenylbutylamino-5-(2-thiophen-2-ylethylsulfamoyl)benzoic acid

HPLC1: Rt=5.253 MS: 491.10

Synthesis Route a) 2,4-Dichloro-5-(2-thiophen-2-ylethylsulfamoyl)benzoic acid from reaction of 2,4-dichloro-5-(chlorosulfonyl)benzoic acid and 2-thiophen-2-ylethylamine according to general procedure, stage 1.
b) 4-Chloro-2-phenylbutylamino-5-(2-thiophen-2-ylethylsulfamoyl)benzoic acid from a) by reaction with phenylbutylamine according to general procedure, stage 2, colorless solid.

EXAMPLE 18

4-Chloro-5-(4-ethylphenylsulfamoyl)-2-phenylbutylaminobenzoic acid

HPLC1: Rt=5.358 MS: 485.17

Synthesis Route a) 2,4-Dichloro-5-(4-ethylphenylsulfamoyl)benzoic acid from reaction of 2,4-dichloro-5-(chlorosulfonyl)benzoic acid and 4-ethylaniline according to general procedure, stage 1.
b) 4-Chloro-5-(4-ethylphenylsulfamoyl)-2-phenylbutylaminobenzoic acid from a) by reaction with phenylbutylamine according to general procedure, stage 2, colorless solid.

EXAMPLE 19

4-Chloro-5-(phenylbutylsulfamoyl)-2-phenylbutylaminobenzoic Acid

HPLC1: Rt=5.511 MS: 523.11

From reaction of 2,4-dichloro-5-(chlorosulfonyl)benzoic acid with phenylbutylamine according to general procedure, stage 2, colorless solid.

EXAMPLE 20

4-Chloro-5-(cyclohexylmethylsulfamoyl)-2-phenylbutylaminobenzoic acid

HPLC1: Rt=5.548 MS: 475.10
Synthesis Route
a) 2,4-Dichloro-5-(cyclohexylmethylsulfamoyl)benzoic acid from reaction of 2,4-dichloro-5-(chlorosulfonyl) benzoic acid and cyclohexylamine according to general procedure, stage 1.
b) 4-Chloro-5-(cyclohexylmethylsulfamoyl)-2-phenylbutylaminobenzoic acid from a) by reaction with phenylbutylamine according to general procedure, stage 2, colorless solid.

EXAMPLE 21

4-Chloro-5-(isobutylsulfamoyl)-2-phenylbutylaminobenzoic acid

HPLC1: Rt=5.208 MS: 437.10
Synthesis Route
a) 2,4-Dichloro-5-(isobutylsulfamoyl)benzoic acid from reaction of 2,4-dichloro-5-(chlorosulfonyl)benzoic acid and isobutylamine according to general procedure, stage 1.
b) 4-Chloro-5-(isobutylsulfamoyl)-2-phenylbutylaminobenzoic acid from a) by reaction with phenylbutylamine according to general procedure, stage 2, colorless solid.

Pharmacological Section
Description of the NBC Activity Measurements

Most of the molecular biology techniques follow protocols from the following publications: "Current Protocols in Molecular Biology (eds. Ausubel, F. M., Brent, R., Kingston, R. E., Moore, D. D., Seidman, J. G., Smith, J. A. and Struhl, K.; John Wiley & Sons)" and "Molecular Cloning: A Laboratory Manual (Sambrook, J., Fritsch, E. F. and Maniatis, T.; Cold Spring Harbor Laboratory Press (1989))".

Firstly, the heart form of human NBC1 was cloned by RT-PCR. After confirmation of the sequence, the corresponding cDNAs were cloned into the vector pcDNA3.1+, which contains the neo gene as a selection marker for eukaryotic cells. For the amplification of the human heart form of NBC1, human heart mRNA (Clontech, Palo Alto, Calif., USA) was amplified using primers which cover the area in which the heart form differs from the kidney form. The heart form in this case differs only at the 5' end of the coding sequence. The area coding for the first 41 amino acids of the kidney form is replaced in the heart form by an area coding for 85 amino acids (positions 118–370 from Abukadze et al., J. Biol. Chem. 273,17689–17695 (1998) or positions 45–294 from Choi et al., Am. J. Physiol. Cell Physiol. 276, C576–C584 (1999) replace positions 150–270 from Burnham et al. (see above.), J. Biol. Chem. 272, 19 111–19 114 (1997). The product of the PCR reaction was first cloned into the vector pCR2.1 and, after verification of the sequence, cloned into the cDNA of the kidney form of NBC1 by means of cleavage sites introduced by means of the PCR reaction. The construct obtained was checked for correct incorporation of the human heart NBC1-cDNA by sequencing. The plasmids obtained for the heart form of human NBC1 were transfected by means of the LipofectAmine™ reagent of the company LifeTechnologies (Gaithersburg, Md., USA) into the cell line CHO K1 (ovary cells of the Chinese hamster), which has no measurable NBC activity. After selection for transfected cells by means of growth in G418-containing medium (only cells which have obtained a neo gene by transfection can survive under these conditions), individual cells were isolated and cultured. Using the test described below, cell clones were identified in FLIPR which have a clear NBC activity. The best cell lines were used for the further tests and, to avoid a loss of the transfected sequence, cultured in G418-containing medium under continuous selection pressure.

For the determination of the inhibitory activity of the active compounds on the heart form of human NBC 1, a test was constructed which represents a further development of the assay constructed for the testing of inhibitors of NCBE ($Na^+$dependent $Cl^-/HCO_{3-}$ exchanger) (EP 0 903 339) based on the acid load method (Sardet et al., Cell 56, 271–280 (1989); Faber et al., Cell. Physiol. Biochem. 6, 39–49 (1996). In this test, the recovery of the intracellular pH ($pH_i$) after prior acidification is determined under conditions in which the NBC is active, the other $pH_i$regulating systems of the CHO cells such as NHE ($Na^+/H^+$ exchanger) and NCBE ($Na^+$-dependent $Cl^-/HCO_{3-}$ exchanger) are blocked, however, by specific inhibitors. In this way, it is ensured that the recovery of the intracellular pH observed is based on the activity of NBC1.

Carrying Out the Measurements

The transfected cells were inoculated into 96 well microtiter plates in a density of about 15,000 cells/well in 200 $\mu$l of growth medium and incubated overnight at 37° C. in a $CO_2$ incubator. The intracellular pH of the transfected cells was determined using the pH-sensitive fluorescent dye BCECF (Molecular Probes (Eugene, Oreg., USA), the precursor BCECF-AM is employed). The cells were first loaded with BCECF-AM. The growth medium of the cells inoculated on the day before was manually removed, since the fetal calf serum present in the medium could interfere with the BCECF staining. For staining, 100 $\mu$l of $NH_4Cl$ stain buffer (20 mM $NH_4Cl$, 115 mM NaCl, 1 mM $MgSO_4$, 1 mM $CaCl_2$, 5 mM KCl, 20 mMHEPES, 5 mM glucose; pH adjusted to 7.4 using 1 M NaOH) was added to the cells of each well, which contains 5 $\mu$M BCECF-AM. The cells were incubated with the stain solution at 37° C. in a $CO_2$ incubator for 20 minutes. During this period of time, on the one hand $NH_4^+$ ions concentrate in the cells, which produces a slight alkalization, and on the other hand BCECF-AM passes into the cells, where, by the action of esterases, the dye BCECF, which is not cell membrane-permeable, were released from BCECF-AM. For the acidification of the cells, these were then thoroughly washed in cell wash water (triple washing with a total volume of 1.2 ml per well) using an $Na^+$- and $NH_4^+$-free wash buffer (133.8 mM choline chloride, 4.7 mM KCl, 1.25 mM $CaCl_2$, 1.25 mM $MgCl_2$, 0.97 mM $K_2HPO_4$, 0.23 mM $KH_2PO_4$, 5 mM HEPES, 5 mM glucose; pH adjusted to 7.4 using 1 M KOH). This washing step leads to a drastic decrease in the intracellular pH (~6.3–6.4). Since the wash buffer, however, contains neither sodium nor bicarbonate ions, the cells were not able to regulate their intracellular pH. The actual measurement of the intracellular pH recovery takes place in the FLIPR (Fluorescence Imaging Plate Reader) of the company Molecular Devices (Sunnyvale, Calif., USA). The FLIPR has an argon laser whose 488 nm band is very highly suitable for the excitation of the BCECF. By means of complicated beam guidance, all 96 wells of a microtiter plate were simultaneously stimulated and can thus be measured simultaneously. Owing to the particular manner of construction of the FLIPR, only those below 50 μm in each well were excited, for which reason adherent cells such as CHO were preferably used. The light emitted from the excited cells first passes through a filter, which is translucent between 510 and 570 nm, and was then recorded by means of a CCD camera. Since the FLIPR also contains an incorporated 96-tip pipettor, the same volume of any desired liquid was simultaneously be pipetted into all 96 wells of a microtiter plate. A total measurement of a complete microtiter plate can be carried out approximately every second. In the FLIPR, 180 μl of substance buffer (90 mM NaCl, 25 mM NaHCO$_3$, 25 mM KCl, 1 mM MgCl$_2$, 1 mM CaCl$_2$, 0.8 mM K$_2$HPO$_4$, 0.2 mM KH$_2$PO$_4$, 10 mM HEPES, 5 mM glucose; on the day of measurement pure CO$_2$ was passed through for 5 seconds and the pH was adjusted to 7.4 using 1 M NaOH; passing through CO$_2$, however, can also be dispensed without the measurement results perceptibly changing) in each case was pipetted into the cells, which were acidified after washing. In order to inhibit the pH regulation systems NHE and NCBE, which are likewise active under these buffer conditions, the substance buffer additionally contained further specific inhibitors of this exchanger. The final concentration of the NHE inhibitor cariporide mesilate (EP 589 336) was 10 μM, that of the NBCE inhibitor according to EP 855 392, Example 1: ethyl 2-butyl-5-methylsulfanyl-3-(2'-cyanaminosulfonyl-biphenyl-4-ylmethyl)-3H-imidazole-4-carbonate 30 μM. After addition of substance buffer, the intracellular pH of the cells acidified beforehand increased as a result of the activity of NBC, which makes itself noticeable in a fluorescence increase of the pH-sensitive dye.

The inhibitory action of a substance is now determined by comparing the fluorescence increase, which behaves linearly to the pH increase, under the influence of this substance with that of wells in which the NBC is uninhibited [100% activity, only addition of cariporide mesilate and of the NCBE blocker according to EP 855 392. Example 1] or is completely inhibited [0% activity, in addition to cariporide mesilate and NCBE blocker according to EP 855 392, Ex. 1, also addition of 400 μM of DCDPC, 4-chloro-2-(3-chlorophenylamino)benzoic acid].

The entire measurement of a microtiter plate lasts two minutes, the entire plate being measured every 2 seconds. After the first 5 measurements, the 180 μl of substance buffer in each case, which contain the compounds to be tested, was pipetted onto the acidified cells at a rate of 60 μl per second. After a few seconds, a clear fluorescence increase was already seen in wells in which the NBC is not inhibited. The region between 20 and 80 seconds, in which the fluorescence increase proceeds linearly in the positive controls, is considered for the calculation of the remaining NBC activity. Of the 96 wells of the microtiter plate, 8 in each case were used for the 100% or the 0% value.

The following data relate to the residual activity at an inhibitor concentration of 10 μM and are the result of duplicate determinations.

| Results: | | [%] at 10 μM |
|---|---|---|
| Example | 1 | 46 |
| | 2 | 56 |
| | 3 | 88 |
| | 4 | 54 |
| | 5 | 78 |
| | 6 | 69 |
| | 7 | 95 |
| | 8 | 89 |
| | 9 | 89 |
| | 10 | 75 |
| | 11 | 81 |
| | 12 | 37 |
| | 13 | 60 |
| | 14 | 87 |
| | 15 | 79 |
| | 16 | 91 |
| | 17 | 95 |
| | 18 | 79 |
| | 19 | 77 |
| | 20 | 89 |
| | 21 | 94 |

What is claimed is:

1. A compound of formula 1,

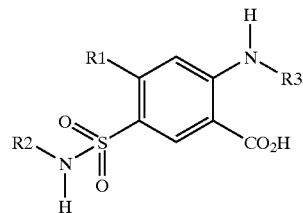

in which:
R(1) is H, Cl, Br, I, CN, (C$_1$–C$_8$)-alkyl, (C$_3$–C$_6$)-cycloalkyl, unsubstituted phenyl, or substituted phenyl where the substituted phenyl is substituted by 1–3 substituents chosen from F, Cl, (C$_1$–C$_3$)-alkyl, methoxy and —(CF$_2$)$_a$—CF$_3$; and
where a is zero, 1, 2 or 3;
R(2) is (C$_1$–C$_8$)-alkyl, —C$_b$H$_{2b}$—(C$_3$–C$_6$)-cycloalkyl, unsubstituted —C$_b$H$_{2b}$-phenyl, substituted —C$_b$H$_{2b}$-phenyl, unsubstituted —C$_b$H$_{2b}$-pyridinyl, substituted —C$_b$H$_{2b}$-pyridinyl, unsubstituted —C$_b$H$_{2b}$-thiophenyl, substituted —C$_b$H$_{2b}$-thiophenyl, unsubstituted —C$_b$H$_{2b}$-furanyl, or substituted —C$_b$H$_{2b}$-furanyl where the substituted —C$_b$H$_{2b}$-phenyl, the substituted —C$_b$H$_{2b}$-pyridinyl, the substituted —C$_b$H$_{2b}$-thiophenyl, and the substituted —C$_b$H$_{2b}$-furanyl are each independently substituted by 1–3 substituents chosen from F, Cl, CF$_3$, (C$_1$–C$_3$)-alkyl, methoxy and —SO$_2$NR(4)R(5);
where R(4) and R(5) independently of one another are H or (C$_1$–C$_4$)-alkyl, and
where b is zero, 1, 2, 3 or 4;
R(3) is unsubstituted —C$_d$H$_{2d}$-phenyl or substituted —C$_d$H$_{2d}$-phenyl,
where the substituted —C$_d$H$_{2d}$-phenyl is substituted by 1–3 substituents chosen from F, Cl, CF$_3$, (C$_1$–C$_3$)-alkyl and methoxy; and
where d is 3 or 4;
or a pharmaceutically tolerable salt thereof, in any stereoisomeric form, or a mixture of any such compounds in any ratio.

2. The compound of the formula I as claimed in claim 1, in which:

R(1) is Cl, $(C_1-C_4)$-alkyl, unsubstituted phenyl, or substituted phenyl
  where the substituted phenyl is substituted by 1–3 substituents chosen from F, Cl, $CF_3$, $(C_1-C_3)$-alkyl and methoxy;

R(2) is $(C_1-C_4)$-alkyl, —$C_bH_{2b}$-cyclohexyl, unsubstituted —$C_bH_{2b}$-phenyl, substituted —$C_bH_{2b}$-phenyl, unsubstituted —$C_bH_{2b}$-pyridinyl, substituted —$C_bH_{2b}$-pyridinyl, unsubstituted —$C_bH_{2b}$-thiophenyl, substituted —$C_bH_{2b}$-thiophenyl, unsubstituted —$C_bH_{2b}$-furanyl, or substituted —$C_bH_{2b}$-furanyl
  where the substituted —$C_bH_{2b}$-phenyl, the substituted —$C_bH_{2b}$-pyridinyl, the substituted —$C_bH_{2b}$-thiophenyl, and the substituted —$C_bH_{2b}$-furanyl are each independently substituted by 1–3 substituents chosen from F, Cl, $CF_3$, $(C_1-C_3)$-alkyl, methoxy and —$SO_2NH_2$; and where b is zero, 1 or 2;

R(3) is unsubstituted -n-$C_4H_8$-phenyl or substituted -n-$C_4H_8$-phenyl,
  where the substituted -n-$C_4H_8$-phenyl is substituted by 1–3 substituents chosen from F, Cl, $CF_3$, $(C_1-C_3)$-alkyl and methoxy;

or a pharmaceutically tolerable salt thereof, in any stereoisomeric form, or a mixture of any such compounds in any ratio.

3. The compound of the formula I as claimed in claim 1, in which:

R(1) is Cl, $(C_1-C_4)$-alkyl, unsubstituted phenyl or substituted phenyl,
  where the substituted phenyl is substituted by 1–3 substituents chosen from F, Cl, $CF_3$, $(C_1-C_3)$-alkyl and methoxy;

R(2) is $(C_1-C_4)$-alkyl, —$C_bH_{2b}$-cyclohexyl, unsubstituted —$C_bH_{2b}$-phenyl, substituted —$C_bH_{2b}$-phenyl, unsubstituted —$C_bH_{2b}$-pyridinyl, substituted —$C_bH_{2b}$-pyridinyl, unsubstituted —$C_bH_{2b}$-thiophenyl, substituted —$C_bH_{2b}$-thiophenyl, unsubstituted —$C_bH_{2b}$-furanyl, or substituted —$C_bH_{2b}$-furanyl
  where the substituted —$C_bH_{2b}$-phenyl, the substituted —$C_bH_{2b}$-pyridinyl, the substituted —$C_bH_{2b}$-thiophenyl, and the substituted —$C_bH_{2b}$-furanyl are each independently substituted by 1–3 substituents selected from the group consisting of F, Cl, $CF_3$, $(C_1-C_3)$-alkyl, methoxy or —$SO_2NH_2$; and where b is 1;

R(3) is unsubstituted -n-$C_4H_8$-phenyl or substituted -n-$C4H_8$-phenyl,
  where the substituted -n-$C_4H_8$-phenyl is substituted by 1–3 substituents chosen from F, Cl, $CF_3$, $(C_1-C_3)$-alkyl and methoxy;

or a pharmaceutically tolerable salt thereof, in any stereoisomeric form, or a mixture of any such compounds in any ratio.

4. The compound as claimed in claim 1, which is 4-chloro-5-(3-chloro-4-fluorobenzylsulfamoyl)-2-phenylbutylaminobenzoic acid;

or a pharmaceutically tolerable salt thereof, in any stereoisomeric form, or a mixture of any such compounds in any ratio.

5. A method for treating arrhythmias comprising administering to a patient in need thereof an effective amount of at least one compound chosen from the compounds as claimed in claim 1.

6. A method for treating or preventing cardiac infarct comprising administering to a patient in need thereof an effective amount of at least one compound chosen from the compounds as claimed in claim 1.

7. A method for treating or preventing angina pectoris comprising administering to a patient in need thereof an effective amount of at least one compound chosen from the compounds as claimed in claim 1.

8. A method for treating or preventing an ischemic condition of the heart comprising administering to a patient in need thereof an effective amount of at least one compound chosen from the compounds as claimed in claim 1.

9. A method for treating or preventing at least one ischemic condition chosen from ischemic conditions of the peripheral nervous system, ischemic conditions of the central nervous system and stroke comprising administering to a patient in need thereof an effective amount of at least one compound chosen from the compounds as claimed in claim 1.

10. A method for treating or preventing at least one ischemic condition chosen from ischemic conditions of a peripheral organ and ischemic conditions of limbs comprising administering to a patient in need thereof an effective amount of at least one compound chosen from the compounds of the formula 1 as claimed in claim 1.

11. A method for treating a state of shock comprising administering to a patient in need thereof an effective amount of at least one compound chosen from the compounds as claimed in claim 1.

12. A method of preserving and storing a transplant for a surgical measure comprising administering to an organ donor an effective amount of at least one compound chosen from the compounds as claimed in claim 1.

13. A method of preserving and storing an organ transplant for surgical measures comprising adding an effective amount of at least one compound chosen from the compounds as claimed in claim 1 to a physiological bath comprising said organ.

14. A method for treating an illness in which cell proliferation is a primary or secondary cause comprising administering to a patient in need thereof an effective amount of at least one compound chosen from the compounds as claimed in claim 1.

15. A method for treating or preventing a disorder of lipid metabolism comprising administering to a patient in need thereof an effective amount of at least one compound chosen from the compounds as claimed in claim 1.

16. A pharmaceutical comprising at least one compound chosen from the compounds as claimed in claim 1 and at least one pharmaceutically acceptable carrier.

* * * * *

UNITED STATES PATENT AND TRADEMARK OFFICE
CERTIFICATE OF CORRECTION

PATENT NO. : 6,593,352 B2
DATED : July 15, 2003
INVENTOR(S) : Weichert et al.

Page 1 of 1

It is certified that error appears in the above-identified patent and that said Letters Patent is hereby corrected as shown below:

<u>Column 17,</u>
Line 51, "-n-C4H$_8$-phenyl," should read -- n-C$_4$H$_8$-phenyl, --.

Signed and Sealed this

Twenty-third Day of September, 2003

JAMES E. ROGAN
*Director of the United States Patent and Trademark Office*